(12) United States Patent
Sasaki

(10) Patent No.: US 9,211,109 B2
(45) Date of Patent: Dec. 15, 2015

(54) ULTRASONIC DIAGNOSTIC DEVICE AND A METHOD OF CONTROLLING THE ULTRASONIC DIAGNOSTIC DEVICE

(75) Inventor: Takuya Sasaki, Nasu-gun (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1207 days.

(21) Appl. No.: 11/852,801

(22) Filed: Sep. 10, 2007

(65) Prior Publication Data

US 2008/0114240 A1  May 15, 2008

(30) Foreign Application Priority Data

Sep. 11, 2006 (JP) ................................. 2006-245699

(51) Int. Cl.
    A61B 8/00 (2006.01)
    A61B 8/06 (2006.01)
    A61B 8/13 (2006.01)
    A61B 8/08 (2006.01)

(52) U.S. Cl.
    CPC . *A61B 8/467* (2013.01); *A61B 8/06* (2013.01); *A61B 8/13* (2013.01); *A61B 8/463* (2013.01); *A61B 8/0883* (2013.01); *A61B 8/0891* (2013.01)

(58) Field of Classification Search
    USPC .......................................... 600/437, 407, 440
    See application file for complete search history.

(56) References Cited

U.S. PATENT DOCUMENTS

| | | | | | |
|---|---|---|---|---|---|
| 4,231,103 | A | * | 10/1980 | Timm | 708/404 |
| 5,501,224 | A | * | 3/1996 | Shiki | 600/456 |
| 5,879,307 | A | * | 3/1999 | Chio et al. | 600/485 |
| 6,050,948 | A | * | 4/2000 | Sasaki et al. | 600/453 |
| 6,293,913 | B1 | | 9/2001 | Tsujino et al. | |
| 2003/0097054 | A1 | * | 5/2003 | Sasaki et al. | 600/407 |
| 2003/0171668 | A1 | * | 9/2003 | Tsujino et al. | 600/407 |
| 2004/0111028 | A1 | * | 6/2004 | Abe et al. | 600/437 |
| 2006/0084873 | A1 | | 4/2006 | Baba et al. | |

FOREIGN PATENT DOCUMENTS

| | | |
|---|---|---|
| JP | 2001-299745 A | 10/2001 |
| JP | 2005-185731 | 7/2005 |

OTHER PUBLICATIONS

Office Action issued Sep. 3, 2013 in Japanese Patent Application No. 2012-021450.

* cited by examiner

*Primary Examiner* — Joel F Brutus
(74) *Attorney, Agent, or Firm* — Oblon, McClelland, Maier & Neustadt, L.L.P.

(57) ABSTRACT

A signal-analysis portion executes a signal-analysis process to signal data that corresponds to an ultrasonic echo received from a subject. A determining portion determines whether image data regarding the subject, which is created based on the signal data upon which said signal-analysis process has been executed, includes a diagnostic target. A parameter-setting portion, based on the determination result, changes to a different value the value of a specific parameter that has an effect on the resolution of the signal-analysis process, among processing parameters to be employed in the signal-analysis process. A display portion displays image data regarding the subject based on the signal data that has been signal-analysis processed according to the specific parameter.

22 Claims, 11 Drawing Sheets

ULTRASONIC DIAGNOSTIC DEVICE AND A METHOD OF CONTROLLING THE ULTRASONIC DIAGNOSTIC DEVICE

BACKGROUND OF THE INVENTION

1. Field of the Invention

The present invention is related to an ultrasonic diagnostic device for performing a signal-analysis process on signal data that corresponds to ultrasonic echoes received from a subject and for creating and displaying image data regarding the subject, and a method of controlling the ultrasonic diagnostic device. In particular, the present invention is related to an ultrasonic diagnostic device for analyzing image data regarding a diagnostic target of said subject, and a method of controlling the ultrasonic diagnostic device.

2. Description of the Related Art

As described in Japanese Unexamined Patent Application Publication 2005-185731, an ultrasonic diagnostic device has been generally known that performs an analysis process, such as an FFT process, on signal data that corresponds to ultrasonic echoes from a subject using an ultrasonic pulse-reflection method or an ultrasonic Doppler method, in order to create and display image data regarding a diagnostic target of the subject, such as waveform data including a tomographic image of a diagnostic site of the subject and blood flow information thereof.

For a diagnosis with this type of ultrasonic diagnostic device, prior to the work for measuring a diagnostic index of the diagnostic target based on the image data regarding the diagnostic target of the subject (e.g. Doppler spectrum waveform data including blood flow information), it is necessary to first perform work for detecting image data corresponding to a diagnostic target of a subject. In other words, in a diagnosis with an ultrasonic diagnostic device, it is common to first go through the detecting phase, which is a phase of work for detecting such image data, before the measuring phase for measuring a diagnostic index based on the detected image data.

A Doppler spectrum waveform that visually represents valve regurgitation of the heart is displayed on the bottom of a display screen on the ultrasonic diagnostic device. The horizontal axis of this waveform indicates time and the vertical axis indicates the blood velocity at each moment. For this waveform, the polarity is set on the negative side (that is, the normal direction of blood flow is negative), and, of the waveforms, the waveform on the positive side represents valve regurgitation of the heart. The flow velocity for this valve regurgitation is fast, but the blood flow volume thereof is minute and the S/N ratio is not necessarily good, so it is assumed to be relatively difficult to detect.

The Doppler spectrum waveform data is created by a fast Fourier transformation (FFT) process. In the FFT process, the Doppler spectrum waveform data is created by extracting waveform data of time periods before and after each instance of sampling (the length of this time period is referred to as the observation time length), performing the FFT process on the waveform data of the time of extraction, calculating the Doppler spectrum of the time of sampling, and ranking the spectrum in chronological order. If the observation time length is not set appropriately for the FFT process, there may be a failure to detect and/or display, for example, a Doppler spectrum waveform on the positive side, (i.e. a waveform corresponding to valve regurgitation).

In the FFT process, there is a trade-off between velocity-detection sensitivity and time resolution. In other words, when the observation time length is set to be relatively long, it is able to obtain spectrums of a wide range of frequencies for the spectrum at each instance of sampling, therefore the velocity-detection sensitivity becomes higher, while the data in the time axis is leveled out and the time resolution decreases. On the other hand, when the observation time length is set to be relatively short, the velocity-detection sensitivity decreases, while the time resolution increases.

With these consideration in mind, it is desirable, in the detecting phase, to set the observation time length to be relatively long to make the velocity-detection sensitivity at each instance of sampling higher, allowing for the easy detection of the waveform, even though the waveform becomes slightly leveled in the time direction. Meanwhile, in the measuring phase for measuring a diagnostic index based on the detected waveform data, it is desirable to set this observation time length to be relatively short to increase the time resolution of the waveform. However, conventional ultrasonic diagnostic devices do not provide such a function for switching the observation time length. Therefore, in the present circumstances, the observation time length is set to be relatively short starting at the detecting phase, while the velocity-detection sensitivity is left to decrease in spite of the detection of waveforms, resulting in that much more time spent detecting the waveforms.

SUMMARY OF THE INVENTION

The first aspect of the present invention is an ultrasonic diagnostic device, comprising a signal-analysis portion configured to execute a signal-analysis process on signal data that corresponds to an ultrasonic echo received from a subject; a determining portion configured to determine whether image data regarding the subject, which is created based on the signal data upon which said signal-analysis process has been executed, includes a diagnostic target; a parameter-setting portion configured to change to a different value the value of a specific parameter that has an effect on the resolution of said signal-analysis process, among processing parameters to be employed in said signal-analysis process, based on said determination result; and a display portion configured to display image data regarding said subject based on the signal data that has been signal-analysis processed according to said specific parameter.

The second aspect of the present invention is a method of controlling an ultrasonic diagnostic device comprising: executing a signal-analysis process on signal data that corresponds to an ultrasonic echo received from a subject; determining whether image data regarding the subject, which is created based on the signal data upon which said signal-analysis process has been executed, includes a diagnostic target; changing to a different value, based on said determination result, the value of a specific parameter that has an effect on the resolution of said signal-analysis process, among processing parameters to be employed in said signal-analysis process; and displaying image data regarding said subject based on the signal data that has been signal-analysis processed according to said specific parameter.

In the first or second aspect of the present invention, before image data regarding the diagnostic target of said subject is obtained, it is possible to detect the image data regarding the diagnostic target while using the parameter that is set to a value that facilitates the detection of image data, resulting in easier detection thereof. Furthermore, after the image data is obtained, it is possible to measure a diagnostic index by employing image data while using the processing parameter that is set to a value that facilitates measurement of the diagnostic index, enabling an accurate measurement of the diag-

DETAILED DESCRIPTION OF THE EMBODIMENTS

Reference will now be made in detail to the present embodiments of the invention, examples of which are illustrated in the accompanying drawings.

Figure 1:
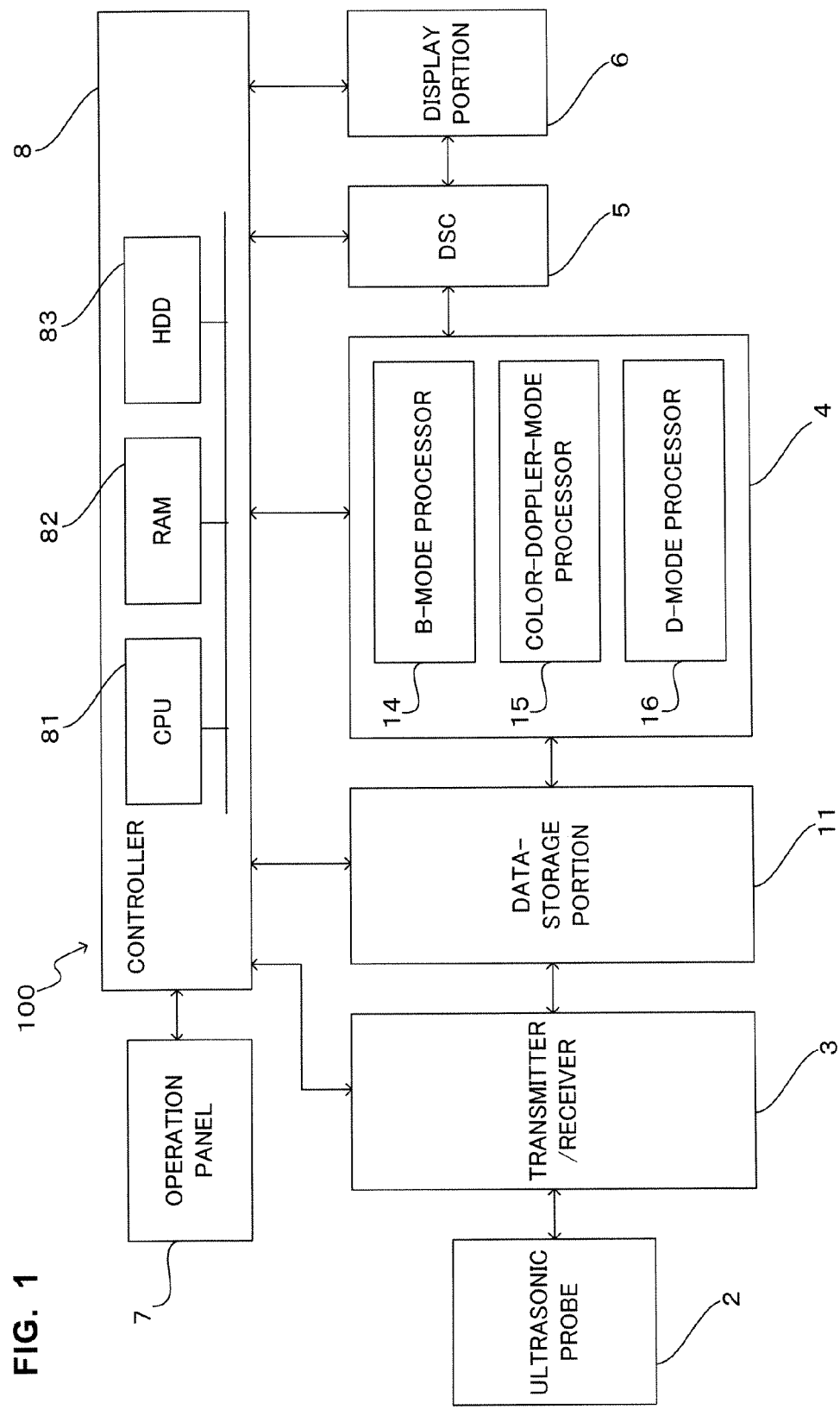
FIG. 1 is a block diagram that shows a schematic configuration of the ultrasonic diagnostic device according to one embodiment of the present invention.

FIG. 1 is a block diagram that shows an overall configuration of the ultrasonic diagnostic device 100 according to the present embodiment. As shown in FIG. 1, the ultrasonic diagnostic device 100 includes an ultrasonic probe 2 for transmitting/receiving ultrasonic waves to/from a subject (not shown), and a display portion 6 for displaying a two-dimensional morphological image (B-mode image) of the subject that has been obtained based on the ultrasonic waves received by the ultrasonic probe 2, a two-dimensional blood-flow image, and a Doppler spectrum waveform.

A transmitter/receiver 3, a signal processor 4, and a Digital Scan Converter (DSC) 5 are provided as a unit for performing signal processing between the ultrasonic probe 2 and the display portion 6. A data-storage portion 11 is provided between the transmitter/receiver 3 and the signal processor 4. Furthermore, the ultrasonic diagnostic device 100 comprises a controller 8 for controlling each of the units 2, 3, 4, 5, and 6. An operation panel 7, which acts as an input-man-machine interface, is connected to this controller 8.

The ultrasonic probe 2 comprises a plurality of piezoelectric transducers such as piezo-ceramics that are arranged thereon. The transmitter/receiver 3 applies a voltage pulse to the plurality of piezoelectric transducers, resulting in the production of ultrasonic waves that will be transmitted to a subject. The ultrasonic probe 2 receives an ultrasonic echo obtained when the transmitted ultrasonic waves reflect back from the subject, and outputs this ultrasonic echo to the transmitter/receiver 3 after converting it into an echo signal that is an electrical signal.

The transmitter/receiver 3 is provided with a pulse generator, a transmission delay circuit, a pulsar, a preamplifier, an A/D, a reception delay circuit, an accumulator, and a phase-detection circuit.

The pulse generator controls the transmission timing of the voltage pulse, generates a timing signal (clock pulse) for each predetermined time period, and transmits the signal to the transmission delay circuit. The transmission delay circuit creates a time difference by delaying the application of the voltage pulse for each piezoelectric transducer and determines the scanning direction of an ultrasonic beam. The pulsar applies a voltage pulse, which has different pulse widths for each mode, to each piezoelectric transducer at a timing received from the transmission delay circuit.

The preamplifier amplifies the echo signal. The A/D converts the amplified signal into a digital signal. The reception delay circuit and the accumulator phase add the signals from each transducer to generate a single signal. The phase-detection circuit outputs digital signal data (Doppler signal), which has been orthogonal-phase-detected, after performing frequency shifting, in which the desired central frequency of the signal that has gone through the accumulator is 0 Hz, to the data-storage portion 11 in a predetermined sampling period.

The data-storage portion 11 comprises a First In First Out (FIFO) memory for saving signals that have been orthogonal-phase-detected. The data-storage portion 11 stores the digital signal data outputted from the transmitter/receiver 3 on the memory thereof in chronological order. In the present embodiment, for ease of explanation, the storage capacity of this memory shall be a capacity that is capable of storing one sheet of images displayed on the display portion 6. Unless the freeze operation to be described later is performed, storage contents of the memory are updated as needed by digital signal data from the transmitter/receiver. The digital signal data stored on the memory is outputted into the signal processor 4 in the order of oldest to newest in said predetermined sampling period. The data-storage portion 11 comprises an external input that is capable of inhibiting or permitting the writing of data.

The signal processor 4 inputs the digital signal data outputted from the data-storage portion 11, and executes signal processing to generate each image based on this digital signal data.

A B-mode processor 14 comprises an echo filter, an envelope-detection circuit, and an LOG, and executes signal processing to generate a two-dimensional morphological image (B-mode signal processing). The echo filter sets a low-pass filter on the signal created by the frequency shifting that has been inputted from the data-storage portion 11. The envelope-detection circuit detects an envelope curve and obtains an envelope-detection signal. The LOG applies a logarithmic conversion to the envelope-detection signal. Data of a two-dimensional morphological image generated in this way is transmitted to the DSC 5.

A color-Doppler-mode processor 15 comprises a corner-turning buffer, a wall filter, an autocorrelator, and an arithmetic portion, and executes signal processing to generate a two-dimensional blood-flow image (CFM-mode signal processing). The corner-turning buffer performs sorting after temporarily storing a row of data of the signals from the orthogonal-phase detection from the phase-detection circuit of the transmitter/receiver 3 (signal obtained via the data-storage portion 11). The wall filter reads, in a predetermined order, the row of data stored on the corner-turning buffer, and removes clutter components in the signal with a predetermined filter band. The autocorrelator performs two-dimensional Doppler-signal processing in real time, and analyzes the frequency of the signal. The arithmetic portion has a mean-velocity-arithmetic portion, a dispersion-arithmetic portion, and a power-arithmetic portion, and they calculate data of the two-dimensional blood-flow image, such as a mean Doppler shift frequency, a dispersion value, or a blood-flow-power value, respectively. For example, the arithmetic portion converts velocity components of blood flow included in the signal into corresponding color information.

Figure 2:
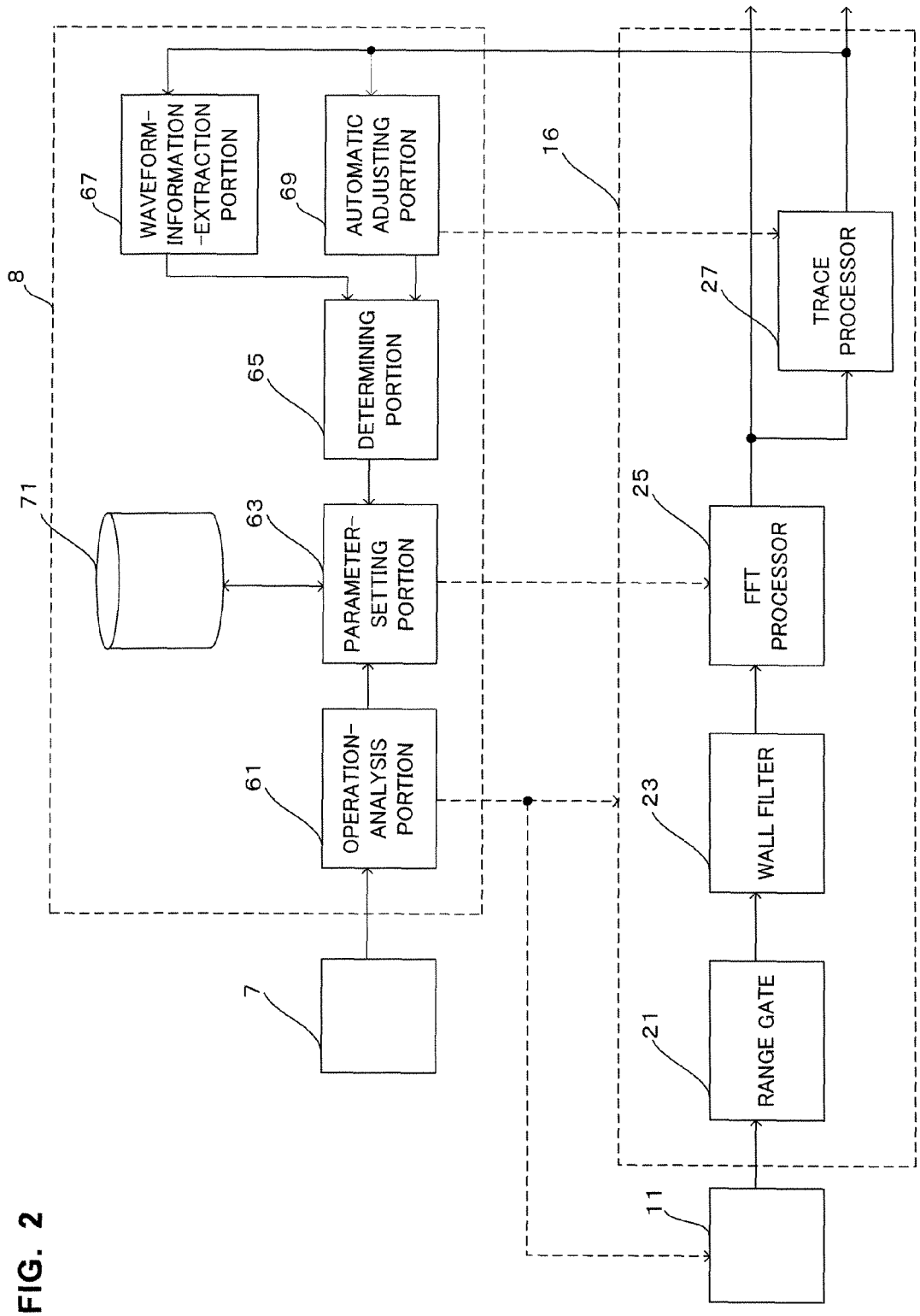
FIG. 2 is a block diagram that shows a detailed configuration of a controller and a D-mode processor.

FIG. 2 shows a detailed configuration of a D-mode processor 16. As shown in FIG. 2, the D-mode processor 16 comprises a range gate 21, a wall filter 23, an FFT processor 25, and a trace processor 27, and executes signal processing for forming Doppler spectrum waveform data (D-mode signal-processing).

The range gate 21 has a sample hold circuit. The range gate 21 samples and holds a Doppler signal at a desired position in the subject according to a sampling pulse equivalent to the range gate. The wall filter 23 removes from the Doppler signal at the desired position relatively slow-moving and undesired low-frequency components (clutter components) coming from a blood vessel wall, a heart wall, or the like.

The FFT processor 25 analyzes the frequency of the Doppler signal from which clutter components have been removed and obtains the spectrum data. Thus, the FFT processor 25 executes signal-analysis processes (e.g. a frequency analysis) on signal data (e.g. the Doppler signal) that corresponds to the ultrasonic echo received from the subject. The spectrum data that is the analysis result is transmitted to the DSC 5. Specifically, the FFT processor 25 obtains waveform data by signal-analysis processing signal data regarding the state of a specific site of the subject, such as the heart. In addition, the FFT processor 25 performs a signal-analysis process to signal data regarding valve regurgitation of the heart.

Figure 3A:
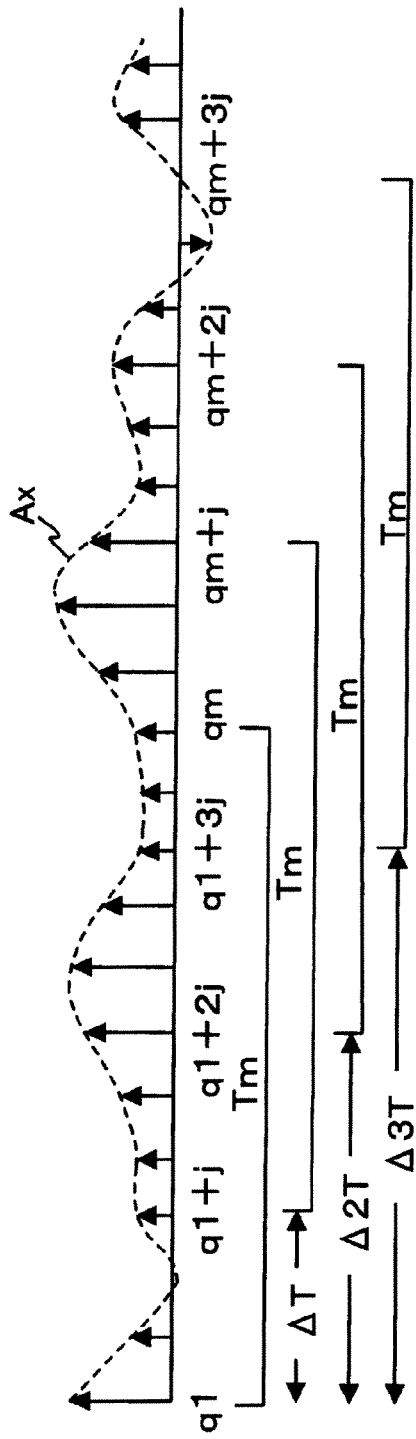
FIGS. 3A and 3B are pattern diagrams for explaining the FFT process.
Figure 3B:
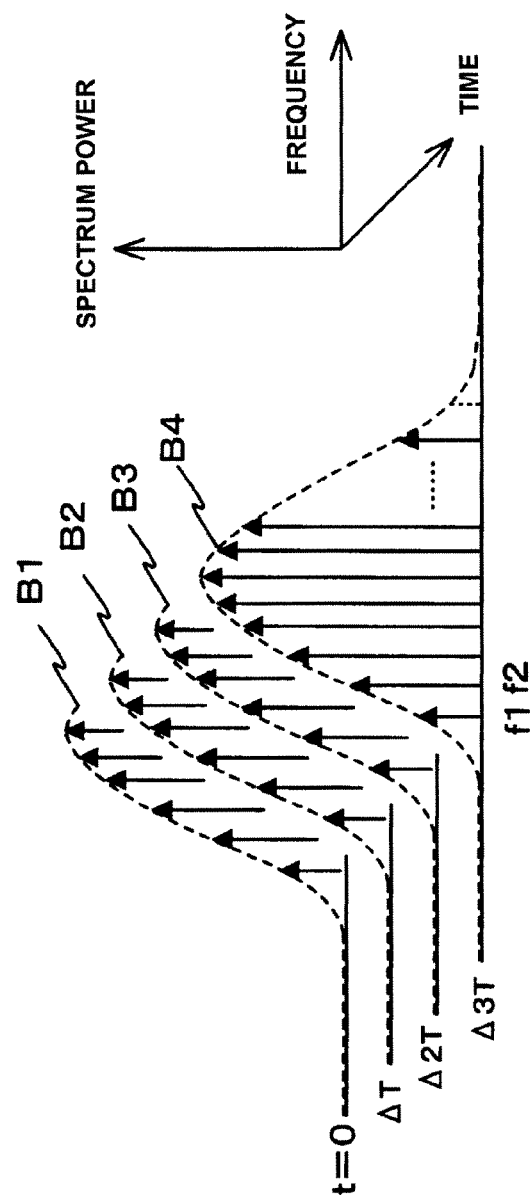

FIGS. 3A and 3B show a typical FFT process conducted by the FFT processor 25. FIG. 3A shows a Doppler signal Ax that is to be inputted to the FFT processor 25, and FIG. 3B shows Doppler spectrum data Bx (x=1, 2, . . . ) that has been obtained by FFT-processing a predetermined zone of this Doppler signal Ax. In this FFT process, for example, m pieces (from q1 through qm) of Doppler signal components (i.e. components with time length of Tm) among the discrete Doppler signals (FIG. 3A) are extracted, which are FFT-processed and the first Doppler spectrum data B1 for the spectrum components p1 through pm is generated. Next, FFT-processed are m pieces of Doppler signals after time ΔT (from q1+j through qm+j), in order to generate new Doppler spectrum data B2. It should be noted that FIG. 3A shows the case of j=3.

Hereinafter, the FFT process will also be performed sequentially to m pieces of Doppler signals, after time 2ΔT (from q1+2j through qm+2j), after time 3ΔT (from q1+3j through qm+3j), . . . in order to generate Doppler spectrum data B3, B4, . . . for the spectrum components p1 through pm in a similar way (FIG. 3B).

The variable m is a processing parameter that the controller 8 can set. Time Tm determined by this m is the time length of a waveform that is extracted to calculate the spectrum at each instance. This time Tm is hereinafter referred to as the observation time length. When this observation time length Tm is set to be long, the Doppler spectrum waveform at each instance of sampling accurately captures the blood flow of a wide range of velocities, thereby increasing the velocity-detection sensitivity, but the time resolution decreases because the data in the time direction is leveled out. In addition, when this observation time length is set to be short, the velocity-detection sensitivity at each instance of sampling decreases, but the time resolution increases.

Meanwhile, the spectrum data outputted from the FFT processor 25 is also transmitted to the trace processor 27. The trace processor 27 creates trace waveform data using the maximum flow velocity Vp (V peak) and the mean flow velocity Vm (V mean) from the inputted spectrum data and outputs the same. This trace waveform data with the maximum flow velocity Vp and the mean flow velocity Vm is also outputted to the DSC 5 and a measuring portion (not shown). In addition, this trace waveform data is employed for measuring diagnostic indexes (HR (Heart Rate), PI, and RI (Resistance Index) of blood flow volume or pulsatile flow) of a diagnostic target of a subject in the measuring portion.

The DSC 5 converts each piece of data outputted from the B-mode processor 14, the color-Doppler-mode processor 15, and the D-mode processor 16 into image signals that can be displayed on the display portion 6 (analog signals of a standard TV scanning) and transmits them to the display portion 6. The DSC 5 thus creates image data regarding a subject based on the signal data to which a signal-analysis process has been executed.

Figure 4:
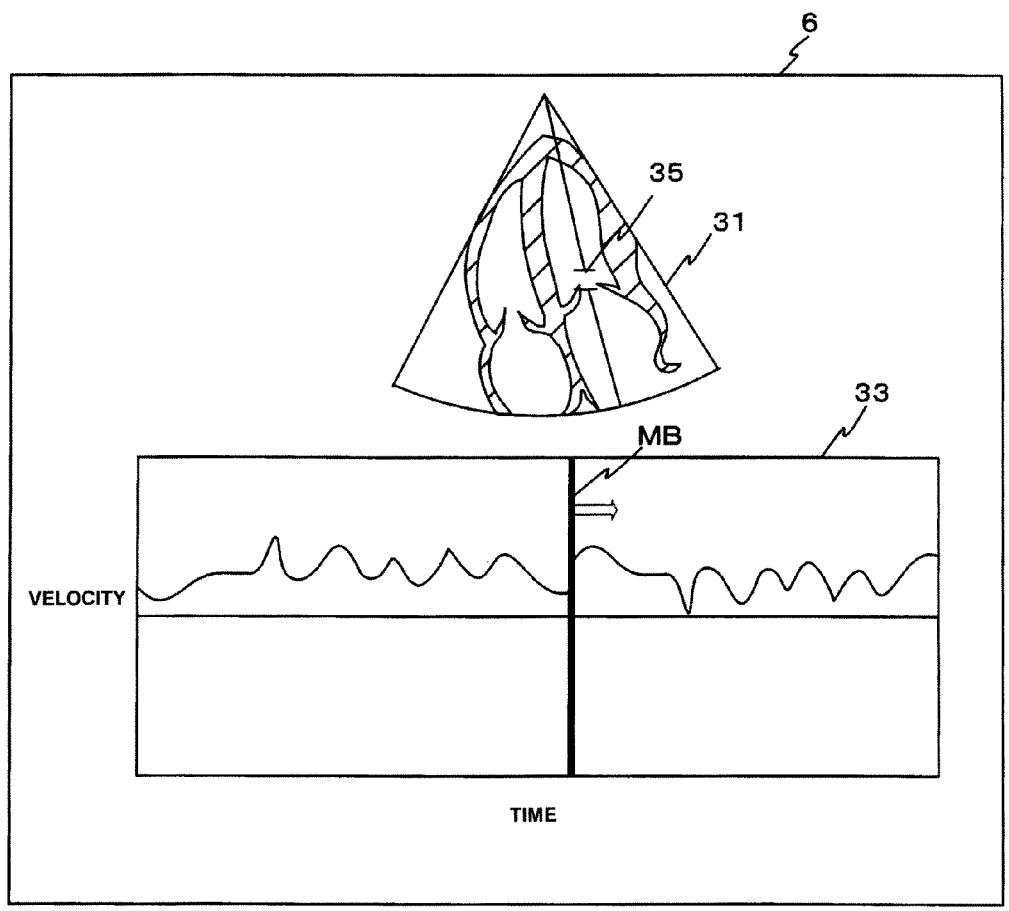
FIG. 4 is a view that shows one example of a display screen displayed by a display portion.

The display portion 6 consists of a monitor, and synthesizes and displays an image corresponding to each image data that has been processed by the DSC 5. In addition, the display portion 6 displays image data regarding the subject based on the signal data which has undergone a signal-analysis process, such as a frequency analysis by the FFT processor 25, according to the processing parameter to be described later. FIG. 4 shows one example of a display screen displayed by the display portion 6. As shown in FIG. 4, this display screen is displayed in a triplex mode. In this display screen, a two-dimensional blood-flow image is displayed overlapping a Region Of Interest (ROI) in a two-dimensional morphological image on a tomographic-image-display portion 31 on the upper side of the screen. FIG. 4 shows a tomographic image of the heart. In addition, a Doppler spectrum waveform (i.e. a time-series data of blood flow) is displayed on a waveform-display portion 33 on the lower side of the screen along with the two-dimensional morphological image. The displayed Doppler spectrum waveform is a waveform corresponding to the position that is indicated in a sample volume 35, which is displayed on the tomographic image in the tomographic-image-display portion 31. When changing the position of this sample volume 35, the timing of the sampling pulse of the range gate 21 is changed, resulting in the display of a Doppler spectrum waveform corresponding to the position of the changed sample volume 35.

The Doppler spectrum waveform is depicted, for example, so as to proceed from the left end to the right end on the waveform-display portion 33 at a constant velocity and with a moving bar MB in the lead. When reaching the right end, the moving bar MB then returns to the left end, and again proceeds to the right end. The waveform display of the Doppler spectrum waveform will be updated in accordance with this moving bar. Such updates of the screen are referred to as scrolls. The update of the velocity range to be described later and the change of the processing parameter are regulated so as to be capable of performing, at the instant when the screen is updated, only at the same time as the update, because the moving bar is on the left side.

The operation panel 7 may consist of a keyboard, a trackball, a mouse, or the like. This operation panel 7 is used by an operator to input the commands for switching between respective modes, switching the position of the ROI and the range gate (sample volume 35), changing the point where the Doppler spectrum waveform data is collected, and the like. In addition, a Freeze ON/OFF button is provided on this operation panel 7 for switching an image displayed on the display portion 6 into either a dynamic image or a static image. When this Freeze ON/OFF button is pressed with a dynamic image displayed, a static image will be displayed on the display portion 6. The button operation at this time is referred to as a freeze operation. In addition, when this Freeze ON/OFF button is pressed with a static image displayed, a dynamic image will be displayed on the display portion 6. The button operation at this time is referred to as a freeze-release operation.

The controller 8 consists of a computer, such as a CPU 81, a RAM 82, and a HDD 83, and a sequencer 84. A control program for the ultrasonic diagnostic device 100 is stored on the HDD 83. The controller 8 reads this control program from the HDD 83 onto the RAM 82 and the CPU 81 executes the control program, thereby accomplishing the functions of an operation-analysis portion 61, a parameter-setting portion 63, a determining portion 65, a waveform-information-calculating portion 67, an automatic adjusting portion 69, or the like, provided in the controller 8 shown in FIG. 2. The operation-analysis portion 61, the parameter-setting portion 63, the determining portion 65, the waveform-information-extraction portion 67, and the automatic adjusting portion 69 are real-time execution tasks that are periodically executed in a predetermined cycle (such as by a timed interruption).

The operation-analysis portion 61 changes a value of the processing parameter when a predetermined instruction, such as an instruction for switching a display image from a dynamic image to a static image, is inputted via a man-machine interface such as the operation panel 7. Specifically, the operation-analysis portion 61 receives information transmitted from the operation panel 7 regarding the operation contents thereof, analyzes the reception result, and performs a process depending on the analysis result. For example, the operation-analysis portion 61 analyzes the operational contents of the operation panel, and if necessary, delivers a parameter-change instruction to the parameter-setting portion 63. In addition, the operation-analysis portion 61 gives to the data-storage portion 11 an instruction for inhibiting or permitting writing into the data-storage portion 11 as necessary. Moreover, the operation-analysis portion 61 is adapted to be capable of transmitting an instruction for re-processing the data stored on the data-storage portion 11 or the like to the signal processor 4.

The parameter-setting portion 63 can change a value of the processing parameter of the FFT processor 25 depending on the parameter-change instruction from the operation-analysis portion 61 or the determining portion 65. Furthermore, the parameter-setting portion 63 can change, based on the determination result from the determining portion 65, the value of the specific parameter that has an effect on the resolution of the signal-analysis process among the processing parameters to be employed in signal-analysis process, into a different value. When the signal-analysis process is the FFT process, this specific parameter includes a time length of the signal data to be extracted to calculate a spectrum at each time point in the FFT process. In the present embodiment, for ease of explanation, the processing parameter of which the value is to be changed, as the specific parameter that has an effect on resolution of the signal-analysis process, shall be only the observation time length Tm described above. Generally, when the observation time length Tm is set to be longer, the Doppler spectrum waveform data corresponding to the diagnostic target is more easily detected by increasing the velocity-detection sensitivity, so the parameter-setting portion 63 will set a relatively large numeric value to be the value of the observation time length Tm in the detecting phase for detecting the waveform data. In addition, when the observation time length Tm is set to be shorter, the time resolution of the waveform becomes higher, so the parameter-setting portion 63 will set a relatively small numeric value as the value of the observation time length Tm in the measuring phase for measuring the diagnostic index. The values of the observation time length Tm for each phase are each pre-stored on the parameter-setting-value-storing portion 71 on the HDD 83. In other words, the parameter-setting portion 63 saves the signal data before the signal-analysis process is applied thereto. The parameter-setting portion 63 is adapted to only have to reference the parameter-setting value stored on this parameter-setting-value-storing portion 71 when changing a value of the parameter. In this case, the controller 8 controls the FFT processor 25 when a predetermined instruction is inputted. In accordance with the instruction from the controller 8, the FFT processor 25 signal-analysis processes, under the processing parameter that has been changed by the parameter-setting portion 63, the signal data that is stored on the parameter-setting-value-storing portion 71. Image data is created accordingly. Also, a display parameter for specifying the display state of the waveform data included in the image data may also be included as a processing parameter. The display parameter of the waveform includes color, for example. Different colors may be used as display parameters so as to display in different colors before and after the freeze. In this case, the display portion 6 displays the waveform data in a display state that is indicated by the display parameter.

The determining portion 65 is provided in order to automatically determine whether it is possible to change the value of the parameter based on the Doppler spectrum waveform or the like. The determining portion 65 determines whether the image data regarding the subject that is created based on the signal data, to which a signal-analysis process has been executed, includes a diagnostic target. In other words, spectrum data can be obtained from the FFT processor 25 and an image is displayed on the display portion 6 according to this spectrum data, so the determining portion 65 determines based on this spectrum data whether this displayed image includes a diagnostic target. The determining portion 65 determines, for example, whether a waveform regarding the diagnostic target has been detected, using features of the diagnostic target of the subject such as the features of the Doppler spectrum waveform data that can be obtained from the waveform-information-extraction portion 67 to be described later, the adjustment state of the automatic adjustment of the display screen received from the automatic adjusting portion 69, or whether the display state of the waveform included in the image data is stable. In the present embodiment, it is determined by analyzing the waveform (i.e. before creating an image) whether a diagnostic target is included. Meanwhile, it is also possible to execute the process for actually creating an image after the FFT process and to determine, from the created image, whether a diagnostic target is included. When the above determination is affirmative, the determining portion 65 then transmits a parameter-change instruction to the parameter-setting portion 63.

The waveform-information-extraction portion 67 inputs the trace data with the maximum flow velocity Vp and the mean flow velocity Vm from the trace processor 27. The waveform-information-extraction portion 67 extracts a feature of a diagnostic target of the subject based on the trace data.

The waveforms corresponding to individual diagnostic targets each have unique features. The waveform-information-extraction portion 67 extracts and outputs these features. Hereinafter, these features of the diagnostic target are specifically explained.

Figure 5A:
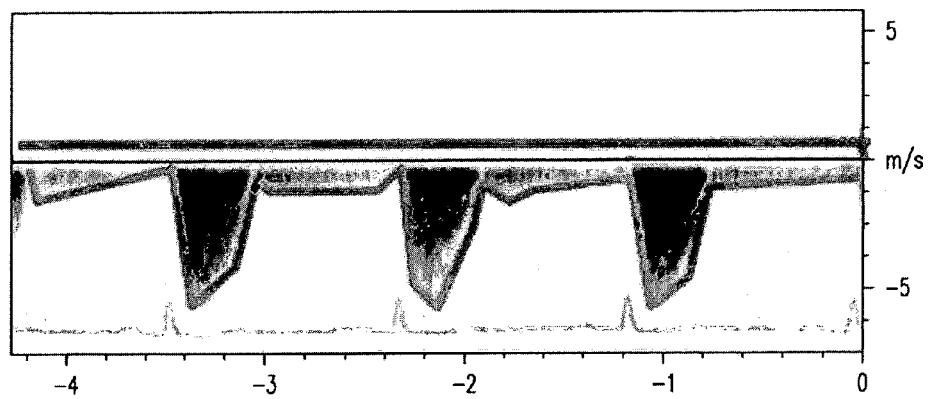
FIG. 5A is one example of a Doppler spectrum waveform and a trace waveform with the maximum flow velocity from which valve regurgitation has not been detected.
Figure 5B:
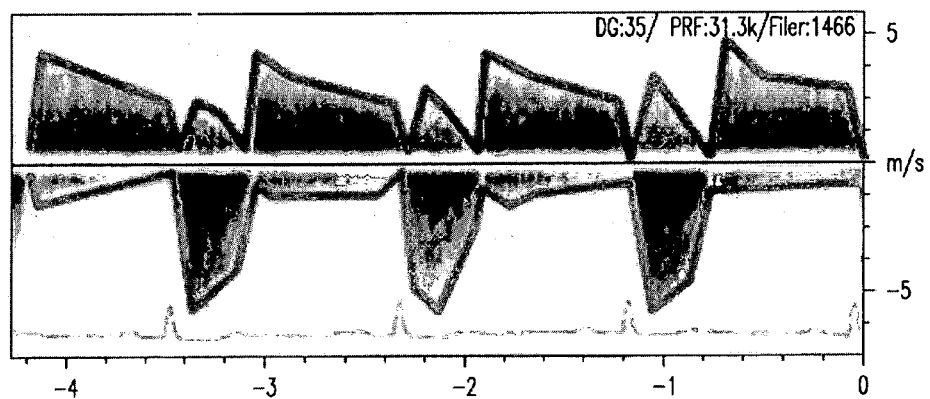
FIG. 5B is one example of a Doppler spectrum waveform and a trace waveform with the maximum flow velocity from which valve regurgitation has been detected.

FIGS. 5A and 5B show a Doppler spectrum waveform corresponding to the blood flow of the valve of the heart.

In the trace waveform data shown in FIG. 5A, peaks appear only on the negative side. Normally, in the Doppler method, a positive sign is given to blood flow in which the direction of the blood flow is toward the ultrasonic probe, and a negative sign is given to blood flow in which the direction thereof recedes from the same. When applying an ultrasonic probe to a certain blood vessel, if the blood vessel is an artery, the velocity of blood flow varies depending on the pulse, but normally slants toward either positive and negative rather than change straddling between positive and negative. Therefore, in the waveform shown in FIG. 5A, the valve flow of the heart is always in the negative direction, so valve regurgitation has not been detected. In this case, among the waveforms of the trace data with the maximum flow velocity Vp on the positive and negative sides that is indicated by a thick line, only one polarity (i.e. only the waveforms of the trace data on the negative side) will exceed a predetermined level.

In the trace waveform data shown in FIG. 5B, peaks appear not only on the positive side but also on the negative side (the horizontal line in the middle indicates that the flow velocity is zero). In this case, there will be forward and reverse flows of blood at the same position (position designated by the sample volume 35). Herein, assuming that the designated position of the sample volume 35 is the valve of the heart, the waveform on the positive side will represent valve regurgitation.

Thus, when the diagnostic target is the heart and there is valve regurgitation thereof, the waveform of the trace data with the maximum flow velocity Vp will exceed a certain level not on one polarity but on both the positive and negative sides. The waveform-information-extraction portion 67 extracts a feature of such a waveform and transmits the same to the determining portion 65.

The automatic adjusting portion 69 receives the trace data with the maximum flow velocity Vp and the mean flow velocity Vm from the trace processor 27. The automatic adjusting portion 69 automatically adjusts, based on the trace data, the velocity range (velocity-display range of the Doppler spectrum waveform) and the baseline (zero-level of the Doppler spectrum waveform) in order to prevent the Doppler spectrum waveform displayed on the display portion 6 from folding back. The automatic adjusting portion 69 extracts trace data for a certain period of time, and calculates a statistical value for the distribution of the maximum flow velocity Vp or the mean flow velocity Vm in the extracted trace data. The automatic adjusting portion 69 then adjusts the velocity range to appropriately display the current Doppler spectrum waveform based on the calculated statistical value. It should be noted that details of the processing by the automatic adjusting portion have been disclosed in, for example, Japanese Unexamined Patent Application Publication 2005-185731, so a detailed explanation is omitted here. The automatic adjusting portion 69 outputs the information regarding the adjusted velocity range or the like to the determining portion 65.

The determining portion 65 receives the information regarding the feature of the waveform that has been extracted by the waveform-information-extraction portion 67, the velocity range received from the automatic adjusting portion 69, or the like, and determines, based on the received information, whether a waveform corresponding to the diagnostic target is detected, or whether the adjustment state is stable.

Next, the processing operations of each portion of the ultrasonic diagnostic device according to the present embodiment are explained in more detail.

Figure 6:
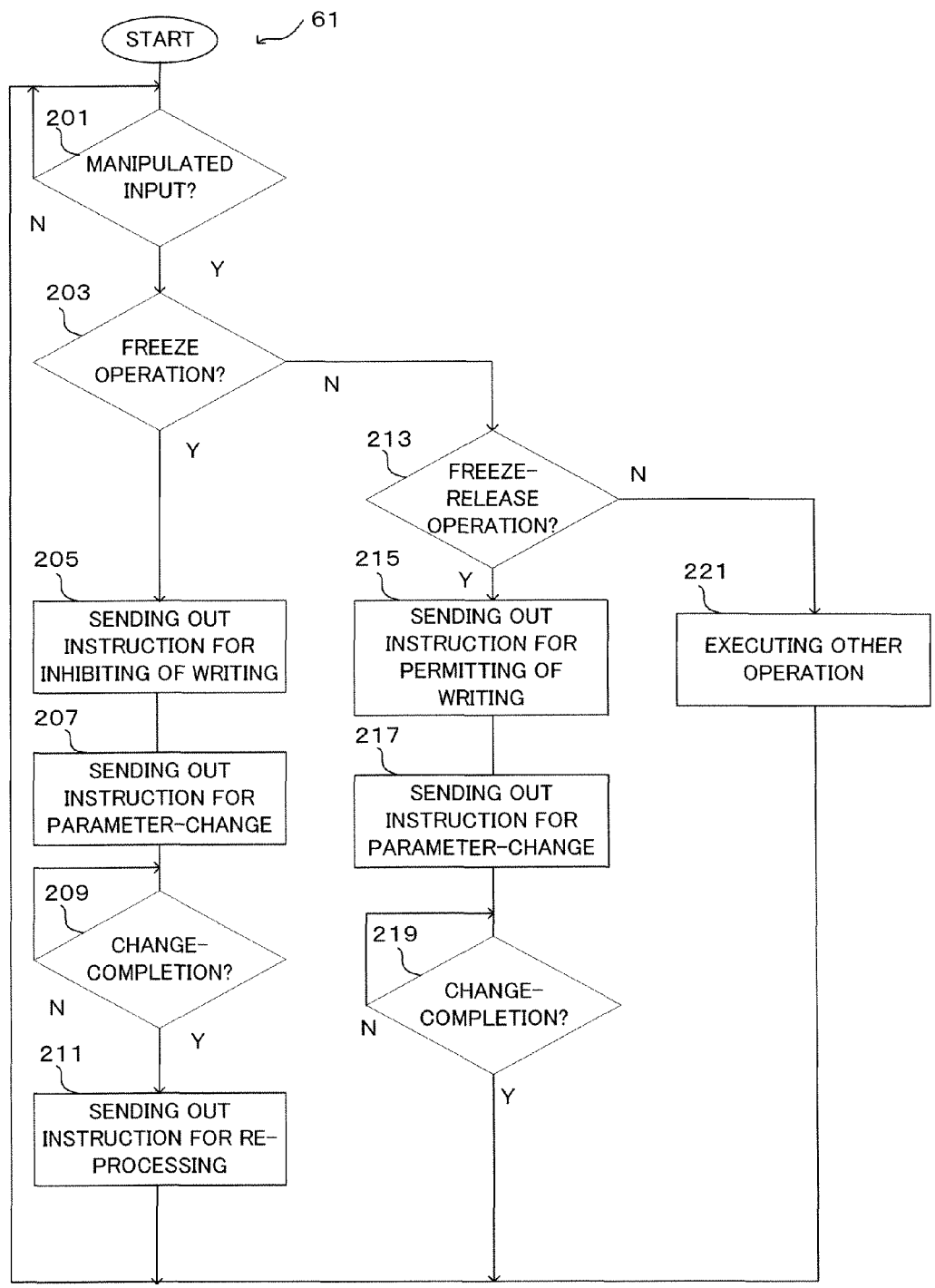
FIG. 6 is a flowchart that shows one example of the processes of an operation-analysis portion.

FIG. 6 shows a flowchart of one example of a process of the operation-analysis portion 61. As shown in FIG. 6, the operation-analysis portion 61 is waiting for a manipulated input at step 201. When there is a manipulated input from the operation panel 7, the operation-analysis portion 61 determines whether the operational content thereof is a freeze operation (step 203). When this determination is affirmed, the process proceeds to step 205, but when denied, it proceeds to step 213.

Steps 205 through 211 are processes followed when the operational content is a freeze operation. The operation-analysis portion 61 first sends out an instruction for the inhibiting of writing into the data-storage portion 11 (step 205). Upon receiving this instruction for the inhibiting of writing, the data-storage portion 11 inhibits the writing of the data inputted from the transmitter/receiver 3 at a predetermined timing. Herein, the predetermined timing is the timing when the waveform of the waveform-display portion 33 on the display portion 6 reaches the right end thereof and the data corresponding to the waveform when the waveform is updated from the left end is written into the memory. This predetermined timing is namely the timing when the first signal data that is employed for the first image data of one sheet of images (e.g., q1 in FIG. 3A) is written into.

At the next step 207, the operation-analysis portion 61 sends out a parameter-change instruction to the parameter-setting portion 63. At step 209, the operation-analysis portion 61 waits for a change-completion notice from the parameter-setting portion 63. Upon receiving this instruction, the parameter-setting portion 63 changes the value of the settings of the processing parameter of the FFT processor 25, as described later. When the change is completed, the parameter-setting portion 63 returns the change-completion notice to the operation-analysis portion 61. Upon the operation-analysis portion 61 receives this, the process proceeds to step 211.

At step 211, re-processing is instructed to the D-Doppler-mode processor 16. Upon receiving this, the D-Doppler-mode processor 16 reads, from the data-storage portion 11 to which writing has been inhibited, the already written data in the order of oldest to newest from the top, and executes re-processing on the range gate 21, the wall filter 23, the FFT processor 25, and the trace processor 27. Therefore, the results of this re-processing (i.e. a static image that is the processing result of the signal data stored on the data-storage portion 11) will be displayed on the display screen of the display portion 6.

On the other hand, when the operational content is determined not to be a freeze operation at step 203, at step 213, it is determined whether the operational content is a freeze-release operation. When this determination is affirmed, the process proceeds to step 215, but when denied, it proceeds to step 221.

Steps 215 through 219 are processed when the operational content is a freeze-release operation. First, at step 213, an instruction for the permitting of writing is sent out to the data-storage portion 11. Upon receiving this, the data-storage portion 11 releases the write-inhibit by the transmitter/receiver 3. The data from the transmitter/receiver 3 is written into the memory from the top thereof. At the next step 215, a parameter-change instruction is sent out to the parameter-setting portion 63. At the next step 217, a change-completion notice is waited for. Upon receiving this, the parameter-setting portion 63 changes the processing parameter of the FFT processor 25 and returns a change-completion notice to the operation-analysis portion 61.

Meanwhile, when the operational content is determined at step 213 not to be a freeze operation but rather another operation, a command processing corresponding to the other operation is executed at step 221.

After step 211, step 219, and step 221 complete, the process returns to step 201, resulting in another wait for manipulated input.

Figure 7:
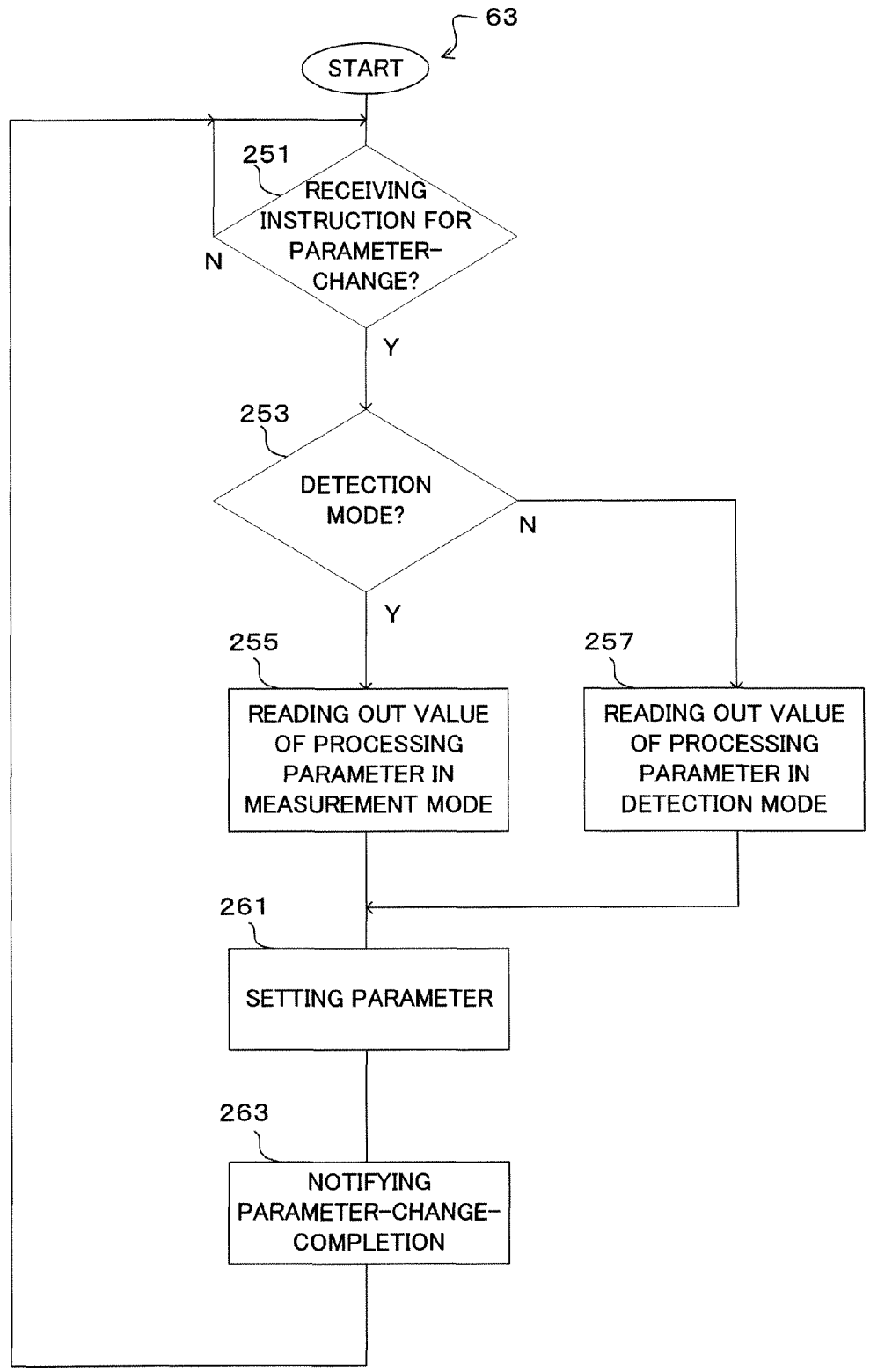
FIG. 7 is a flowchart that shows one example of the processes of a parameter-setting portion.

Next, the operations of the parameter-setting portion 63 are explained. FIG. 7 shows a flowchart of one example of a process of the parameter-setting portion 63. As shown in FIG. 7, the parameter-setting portion 63 is first waiting to receive a change instruction at step 251. As described above, when receiving a parameter-change instruction from the operation-analysis portion 61 or the like, the process proceeds to step 253. At step 253, it is determined whether a detection mode is set. The parameter-setting portion 63 is currently managing internally whether it is a mode in the detecting phase for detecting a waveform corresponding to a diagnostic target (i.e. detection mode) or if it is a mode in the measuring phase for measuring a diagnostic index (i.e. measurement mode) so this determination is made by referencing the management information thereof.

When the determination at step 253 is affirmed, the process proceeds to step 255, but when denied, it proceeds to step 257. At step 255, a value of the processing parameter in the measurement mode (i.e. a relatively small value for the observation time length Tm) is read from the parameter-setting-value-storing portion 71 in order to switch over from the detection mode to the measurement mode. In addition, at step 257, a value of the processing parameter in the detection mode (i.e. a relatively large value for the observation time length Tm) is read from the parameter-setting-value-storing portion 71 in order to switch over from the measurement mode to the detection mode.

At the next step 261, the read setting value of the observation time length Tm is set to the FFT processor 25, thereby changing the value of the observation time length Tm of the FFT process. At the next step 263, a change-completion notice is returned to the source of the parameter-change instruction (such as the operation-analysis portion 61). After completion of step 263, the process returns to step 251 again, resulting in another wait for a parameter-change instruction.

Figure 8A:
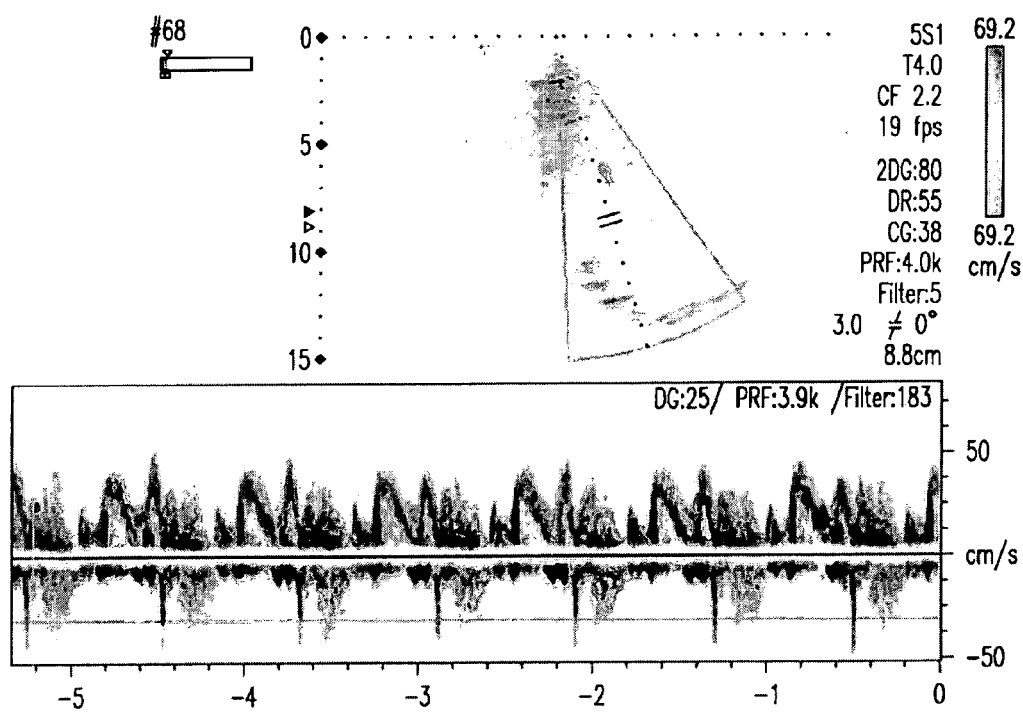
FIG. 8A is a view that shows one example of a waveform display in the detecting phase.
Figure 8B:
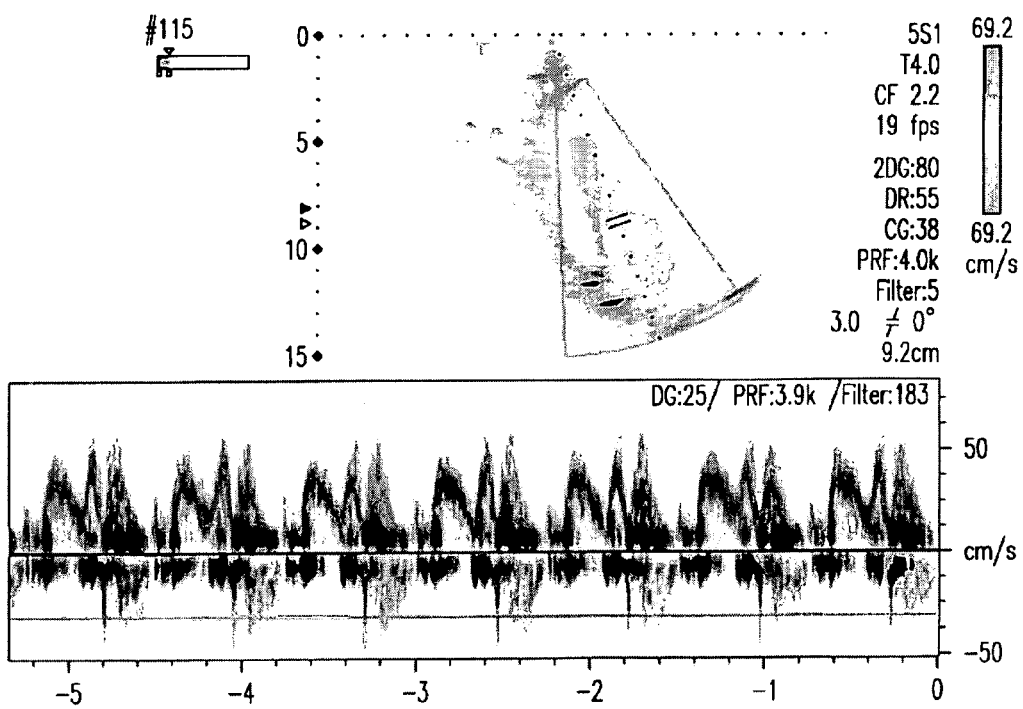
FIG. 8B is a view that shows one example of a waveform display in the measuring phase.

FIG. 8A shows one example of a display screen of the display portion 6 prior to a freeze operation, and FIG. 8B shows one example of the display screen of the display portion 6 after the freeze operation. As shown in FIGS. 8A and 8B, the value of the processing parameter (observation time length Tm) of the FFT processor 25 is changed between before and after the freeze operation, so it can be seen that the displayed Doppler spectrum waveform data is significantly different from each other.

Figure 9:
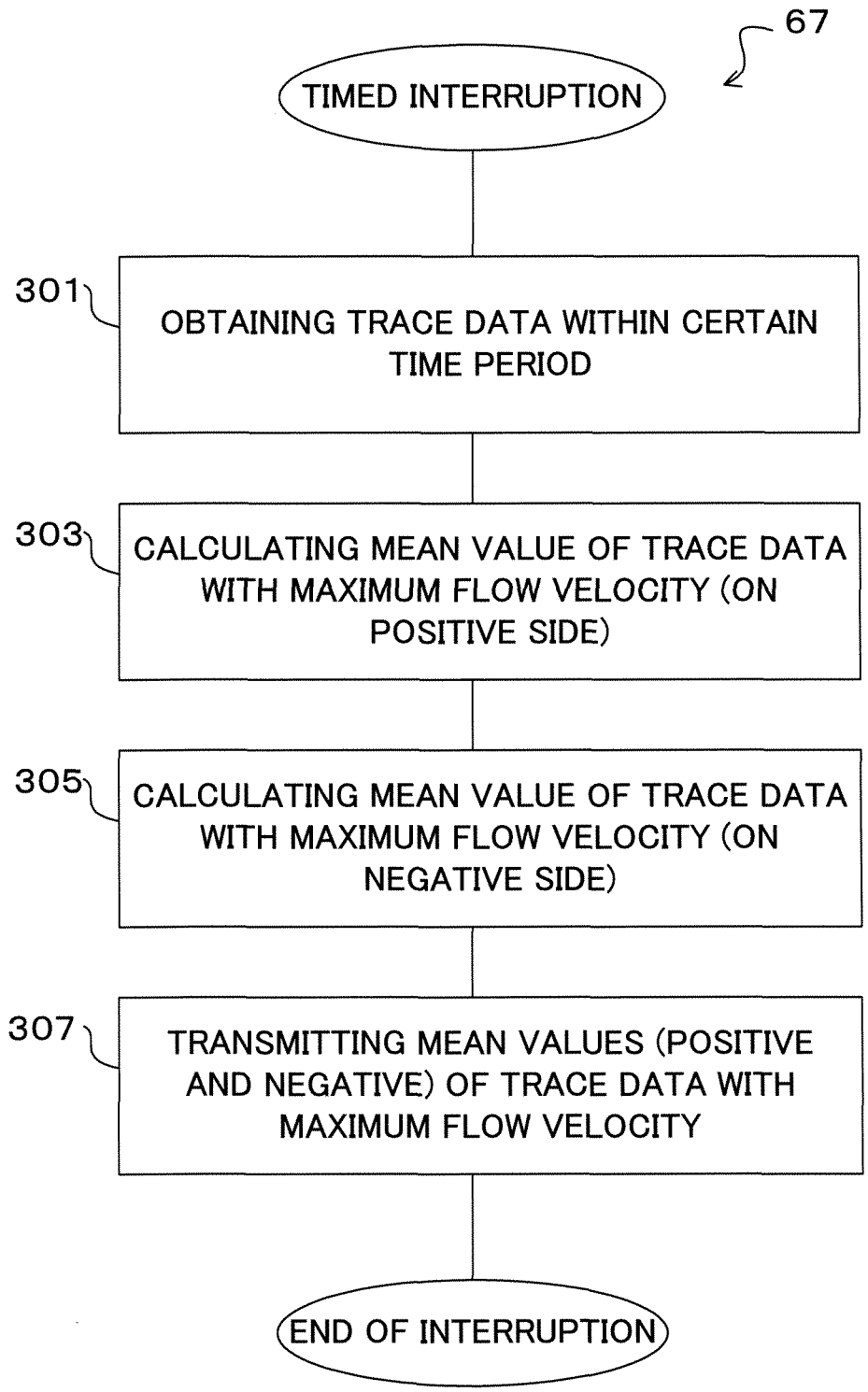
FIG. 9 is a flowchart that shows one example of the processes of a waveform-information-extraction portion.

Next, the operations of the waveform-information-extraction portion 67 are explained. FIG. 9 shows a flowchart of one example of a process of the waveform-information-extraction portion 67. The process shown in FIG. 9 is a process in which a diagnostic target is valve regurgitation of the heart and the information regarding the features thereof is extracted.

In FIG. 9 again, the waveform-information-extraction portion 67 starts with a periodic timed interruption. First, at step 301, trace data within a certain time period is obtained from the trace processor 27. At the next step 303, the mean value of the trace data with the maximum flow velocity on the positive side is calculated, and at the next step 305, the mean value of the trace data with the maximum flow velocity on the negative side is calculated. At the next step 307, the mean values (positive and negative) of the trace data with the maximum flow velocity Vp are transmitted to the determining portion 65, which is the end of the process.

Figure 10:
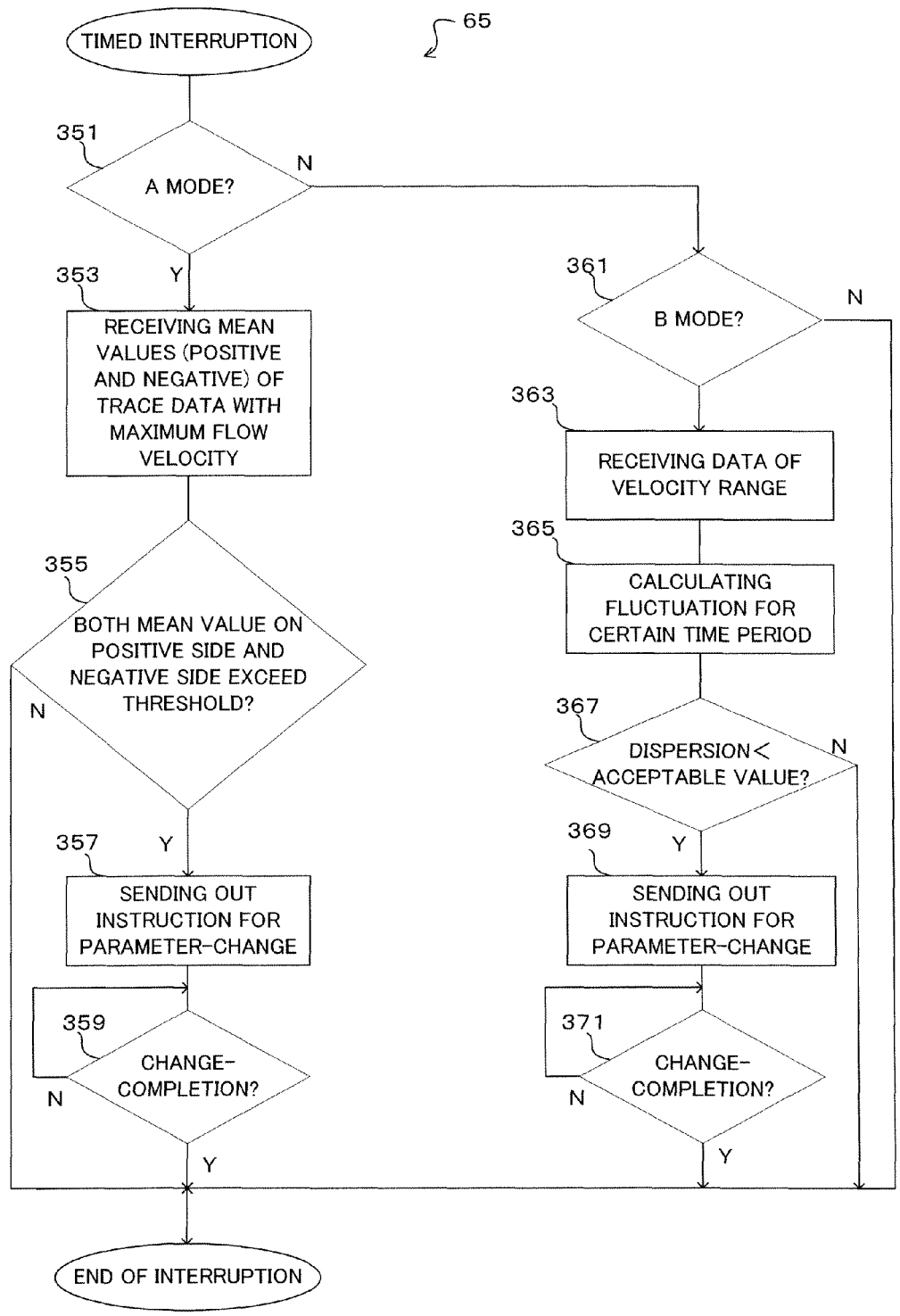
FIG. 10 is a flowchart that shows one example of the processes of a determining portion.
Figure 11:
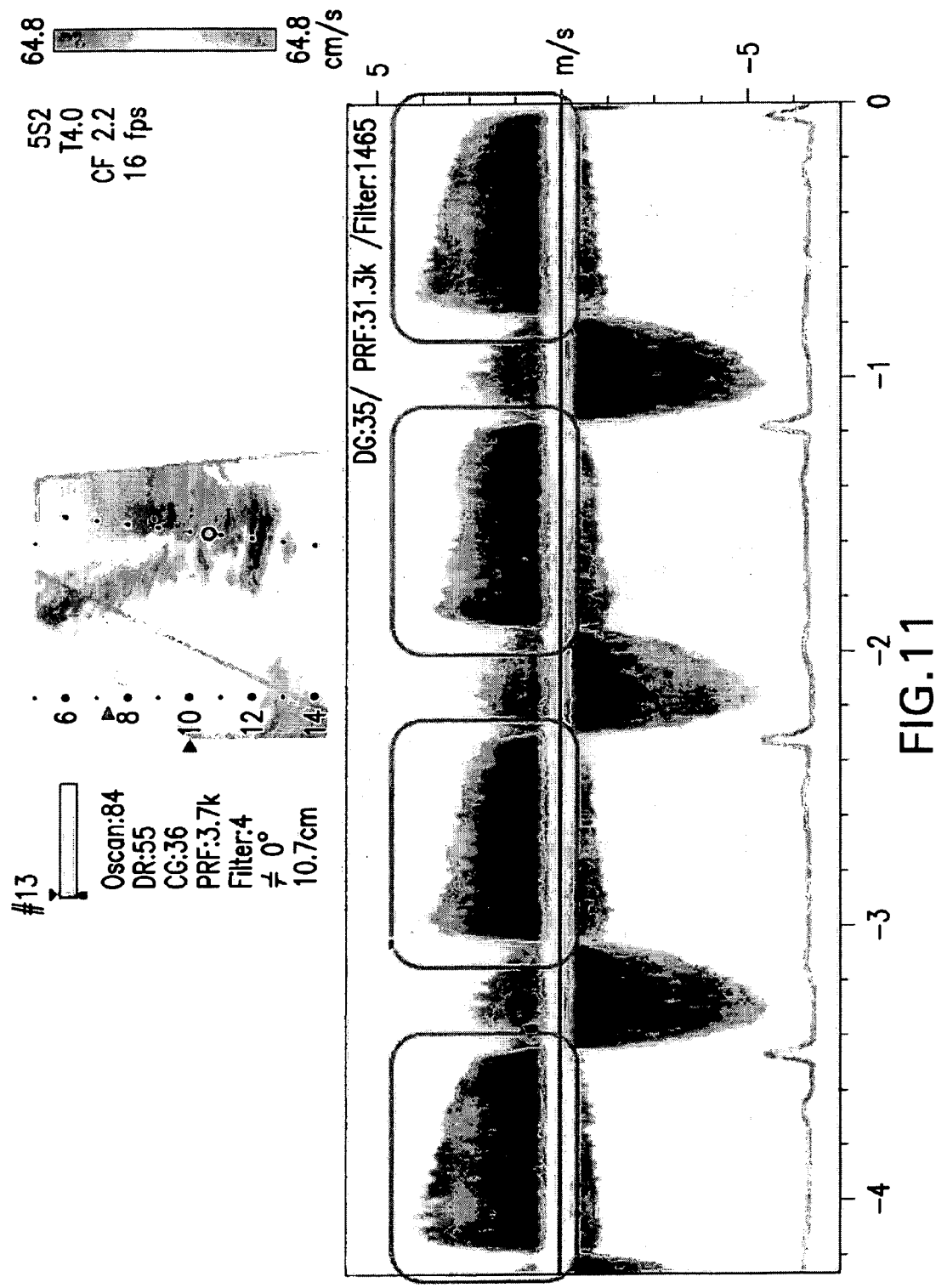
FIG. 11 is a view that shows a Doppler spectrum waveform of valve regurgitation of the heart.

Next, the operations of the determining portion 65 are explained. FIG. 10 shows a flowchart of one example of a process of a determining portion 65. Processing modes of the determining portion 65 include an A mode and a B mode. The A mode is a mode for determining whether it is possible to change the processing parameter based on the information transmitted from the waveform-information-extraction portion 67, and the B mode is a mode for determining the possibility of changing the processing parameter based on the information transmitted from the automatic adjusting portion 69. Both the A mode and B mode shall be preset by the device parameter.

As shown in FIG. 10, the determining portion 65 starts a process with a periodic timed interruption. First, at step 351, it is determined whether the processing mode is set to the A mode. When this determination is affirmed, the process proceeds to step 353, but when denied, it proceeds to step 361.

Processes at steps 353 through 359 are processes followed when the A mode is set. First, at step 353, the mean values of the (positive and negative) trace data with the maximum flow velocity are received. At the next step 355, it is determined whether both the mean value of the trace data with the maximum flow velocity on the positive side and the mean value of the trace data with the maximum flow velocity on the negative site exceed the threshold. When this determination is affirmed, a parameter-change instruction is sent out to the parameter-setting portion 63 at step 357, and a change-completion notice thereof is waited for step 359. Upon receiving this, the parameter-setting portion 63 changes the processing parameter of the FFT processor 25 and returns the change-completion notice. Upon receiving this change-completion notice, the determining portion 65 ends the process. When the determination is denied at step 355, the process ends there.

On the other hand, when the determination is denied at step 355, the process ends without sending any parameter-change instruction.

Processes at steps 361 through 371 are processes followed when the B mode is set. First, at step 361, it is determined whether the mode is set to the B mode. When this determination is affirmed, the process proceeds to step 363, but when denied, the process ends.

At step 363, data of the velocity range that is outputted from the automatic adjusting portion 69 is received. At the next step 365, a fluctuation of the velocity range for a certain time period (e.g. dispersion) is calculated. At the next step 367, it is determined whether the dispersion is within an acceptable value. When this determination is affirmed, the process proceeds to step 369, in which a parameter-change instruction is sent, and then to step 371, where the receipt of a change-completion notice is waited for. Upon receiving this, the parameter-setting portion 63 changes the processing parameter of the FFT processor 25 and returns a change-completion notice. Upon receiving this change-completion notice, the determining portion 65 ends the process.

On the other hand, when the determination is denied at step 367, the process ends there.

As described above, the controller 8 changes the value of the processing parameter in the FFT processor 25 (the value of the observation time length Tm) based on the freeze operation or freeze-release operation inputted from the operation panel 7, the waveform information that is extracted by the waveform-information-extraction portion 67, and the information regarding the adjustment state in the automatic adjusting portion 69. Incidentally, the possibility of changing the parameter is determined on the basis of the dispersion of the velocity range in the process in the B mode (steps 363 through 371), but it is possible to employ another statistical value that indicates the magnitude of the variation of the velocity range (such as a standard deviation) instead of the dispersion of the velocity range.

Next, an operational flow of a diagnosis employing the ultrasonic diagnostic device 100 that has the configurations and operations described above is explained.

First, a diagnostic method in which a freeze operation is performed is explained. At the first time point, an operator applies the ultrasonic probe 2 to a subject and performs an alignment of the sample volume 35 to a diagnostic target site while observing a tomographic image displayed on the tomographic-image-display portion 31 of the display portion 6. At the alignment, the waveform-display portion 33 is checked to verify whether the waveform data that should be obtained is displayed. This phase is still the detecting phase of the waveform, so a relatively large value is set as the processing parameter for the FFT process (observation time length Tm) so as to easily detect the waveform. This enables the operator to detect the waveform data using high velocity-detection sensitivity.

When waveform data corresponding to the diagnostic target is displayed on the waveform-display portion 33 and it is confirmed that the waveform data has been obtained, the operator presses the Freeze ON/OFF button on the operation panel 7. When the operational contents are transmitted to the operation-analysis portion 61 by pressing this Freeze ON/OFF button, a parameter-change instruction is transmitted to the parameter-setting portion 63 and the value of the processing parameter for the FFT process (observation time length Tm) is changed to a relatively short value. This makes it possible to create the FFT-processed waveform data (static image) using a processing parameter that provides a high time resolution and to measure a diagnostic index with high accuracy by employing this waveform data.

Next, a diagnostic method employing the A mode (parameter change by the waveform-information-extraction portion) is explained. At the first time point, an operator applies the ultrasonic probe 2 to a subject and performs an alignment of the sample volume 35 to a diagnostic target site while observing a tomographic image displayed on the tomographic-image-display portion 31 of the display portion 6. At the alignment, the waveform-display portion 33 is checked to verify whether the waveform data that should be obtained is displayed. This phase is still the detecting phase of the waveform, so a relatively large value is set as the processing parameter for the FFT process (observation time length). This enables the operator to detect the waveform data using high velocity-detection sensitivity.

When the sample volume 35 is set appropriately and features indicating valve regurgitation emerge in the waveform data, the mean values of both the positive and negative trace data with the maximum flow velocity that have been extracted by the waveform-information-extraction portion 67 will exceed the threshold, so the determining portion 65 sends a parameter-change instruction to the parameter-setting portion 63. Upon receiving this, the parameter-setting portion 63 changes the value of the processing parameter (observation time length Tm). This makes it possible to create FFT-processed waveform data that uses a processing parameter that provides a high time resolution and to measure a diagnostic index with high accuracy by employing this waveform data.

Next, a diagnostic method employing the B mode (parameter change by the adjustment state of the automatic adjustment) is explained. At the first time point, an operator applies the ultrasonic probe 2 to a subject and performs an alignment of the sample volume 35 to a diagnostic target site while observing a tomographic image displayed on the tomographic-image-display portion 31 of the display portion 6. At the alignment, the waveform-display portion 33 is checked to verify whether the waveform data that should be obtained is displayed. This phase is still the detecting phase of the waveform, so a relatively large value is set as the processing parameter for the FFT process (observation time length Tm). This enables the operator to detect the waveform data using high velocity-detection sensitivity.

The automatic adjusting portion 69 adjusts the velocity range based on the trace waveform with the maximum flow velocity Vp and mean flow velocity Vm that is obtained from the trace processor 27, and outputs the adjusted value to the determining portion 65. When the dispersion indicating the varying state of the velocity range falls within an accepted range, the determining portion 65 determines that the waveform data has been detected and sends a parameter-change instruction to the parameter-setting portion 63, and the parameter-setting portion 63 changes the value of the processing parameter (observation time length) to a relatively small value. This makes it possible to create FFT-processed waveform data that uses a processing parameter that provides a high time resolution and to measure a diagnostic index with high accuracy by employing this waveform data.

As described above in detail, in the present embodiment, before waveform data regarding the diagnostic target of the subject is obtained, at the signal processor 4 for the signal data that corresponds to the echo signal from the diagnostic target of the subject, it is possible to detect the waveform regarding the diagnostic target under a processing parameter (observation time length Tm) that is set to a value that facilitates the detection of the waveform and results in easier detection thereof. Furthermore, after image data has been obtained, it is possible to measure a diagnostic index by employing waveform data under a processing parameter (observation time length Tm) that is set to a value that facilitates the measurement of the diagnostic index, enabling accurate measurement of the diagnostic index. Therefore, even in a case of a minutely small amount of Doppler spectrum signals, detection becomes easier and the time spent on detection is shortened, so ultrasonic diagnostics conducted with high accuracy and in a short time is achieved.

In addition, in the ultrasonic diagnostic device 100 according to the present embodiment, the parameter-setting portion 63 changes the value of the observation time length Tm when a switching operation is performed on the operation panel 7. When configured in this way, the operator who determines that a waveform has been detected uses the operation panel 7 for a switching operation and the value of the processing parameter is automatically changed with the operation, thereby resulting in a significant improvement in the operability of the device.

Moreover, in the ultrasonic diagnostic device 100 according to the present embodiment, the parameter change is performed by a freeze operation for switching the image to be displayed from a dynamic image to a static image. This freeze operation is normally performed after detecting the waveform, so the work burden for the operator will be significantly reduced by configuring the value of the processing parameter to change automatically in conjunction with this freeze operation.

In addition, in the ultrasonic diagnostic device 100 according to the present embodiment, data that has not yet been processed by the D-mode process is saved on the data-storage portion 11. When switching the image to be displayed from a dynamic image to a static image, the D-mode processor 16 of the controller 8 creates waveform data by performing again the predetermined process on the signal data that is stored on the data-storage portion 11 using the observation time length Tm, the value of which was changed by the parameter-setting portion. When configured in this way, even in the case of the waveform data to which the FFT process has already been applied under a long observation time length Tm, it becomes possible to display it again on the screen of the display portion 6 by setting the observation time length Tm to be short and repeating the D-mode process.

Moreover, in the ultrasonic diagnostic device 100 according to the present embodiment, the waveform-information-extraction portion 67 extracts the features of the waveform data. The determining portion 65 then determines whether the extracted features correspond to the features of the diagnostic target of the subject. When the determination of the determining portion 65 is affirmative, the parameter-setting portion 63 then changes the value of the processing parameter. When configured in this way, the processing parameter will be automatically changed after the detection of the waveform data of the diagnostic target based on the feature of the waveform, thereby significantly reducing the work burden for the operator.

Incidentally, valve regurgitation of the heart was the diagnostic target and the feature that appears in the waveform data thereof was extracted to confirm the detection of the waveform in the above embodiment, but such features of waveforms vary depending on diagnostic targets. Therefore, the waveform-information-extraction portion 67 has to extract waveform information specific to each diagnostic target, and the determining portion has to perform determination processes according to the features of the waveform.

In addition, in the ultrasonic diagnostic device 100 according to the present embodiment, the automatic adjusting portion 69 automatically adjusts the display state of the waveform based on the size of the waveform data. The determining portion 65 then determines whether the adjustment state by the automatic adjusting portion 69 is stable. Furthermore, when the determination of the determining portion 65 is affirmative, the parameter-setting portion 63 changes the value of the processing parameter. This configuration allows the processing parameter to be automatically changed when the adjustment state of the automatic adjusting portion 69 is stable, thereby significantly reducing the work burden for the operator.

Incidentally, in the ultrasonic diagnostic device 100 according to the above embodiment, the processing parameter of which the value would be changed was the observation time length Tm in the FFT processor, but the present invention is not limited to this, and all processing parameters related to the resolution of the signal processor 4 are potential targets of change. For example, the sampling interval $\Delta T$ shown in FIG. 3A is one example of a parameter to be changed.

The processor in which the processing parameters can be changed is not limited to the FFT processor 25. For example, it may also be adapted to change the time length of the waveform data to be extracted for calculating the maximum flow velocity Vp in the trace processor 27. Furthermore, it may also be adapted to change the processing parameter of the B-mode processor 14 and the color-Doppler-mode processor 15.

Also, changeable parameters may also include display parameters on the display portion 6, such as a pixel ratio and display colors. For example, a color parameter can be included as a processing parameter, and the display portion 6 displays a waveform according to the color indicated by this color parameter. In other words, when the color parameter indicates blue, the waveform is displayed in blue, and when the color parameter indicates red, the waveform is displayed in red. The parameter-setting portion 63 then changes the color parameter between before and after the freeze operation. For example, the color parameter may be blue before the freeze operation and red after the freeze operation. It is possible to visually present that different waveforms are obtained before and after the freeze operation by changing the display color between before and after the freeze operation in this way.

In addition, in the above embodiments, as the number of parameters to be changed, one in the phase for detecting a waveform was provided while one in the phase for measuring a diagnostic index was provided. However, the present invention is not limited to this, and a plurality of parameters to be changed may be provided for each phase. When configured in this way, it is also possible to select the optimal setting values from a plurality of setting values for each phase. At this time, after the freeze operation, while switching over the values of the parameter in order of precedence, it may also be adapted to repeat the D-mode process on the signal data stored on the data-storage portion 11, to display on the display portion 6, and to select the optimal processing parameters corresponding to the best waveform data. It should be noted that, such processes require a man-machine interface for switching over the processing parameter in addition to the Freeze ON/OFF button on the operation panel 7.

Incidentally, in the above embodiments the data-storage portion 11 was arranged between the transmitter/receiver 3 and the signal processor 4, but the present invention is not limited to this, and it may be adapted to provide a data-storage portion in each processor 14, 15, and 16 of the signal processor 4. In this case, the D-mode processor 16 is provided with a data-storage portion between the wall filter 23 and the FFT processor 25. In other words, the data-storage portion only has to be provided on the front stage of the processor corresponding to the processing parameter in which the value is changed.

In addition, in the above embodiments the display mode of the display portion 6 was set to the triplex mode, but the present invention is not limited to this. Needless to say, the Doppler spectrum waveform may be singularly displayed.

Moreover, the ultrasonic diagnostic device 100 according to the above embodiments employed the pulse-Doppler method for calculating the Doppler spectrum waveform, but it is entirely possible to apply the present invention to the continuous-wave Doppler method.

Incidentally, the piezoelectric transducer was employed as an ultrasonic transducer in the above embodiments, but a Capacitive Micromachined Ultrasonic Transducer (CMUT), which has become capable of fabricating a vibrating portion on a silicon substrate due to recent developments in MEMS technology, may be employed as an ultrasonic transducer.

The embodiments and various modified examples described above do not limit the scope of the present invention. Therefore, those skilled in the art can adopt embodiments in which each element or all elements are replaced with the equivalent thereof, but these embodiments is also included in the scope of the present invention.

What is claimed is:

1. An ultrasonic diagnostic device, comprising:
Fourier processing circuitry configured to execute a signal-analysis process on signal components having time length Tm among signal data that corresponds to an ultrasonic echo received from a subject, the signal-analysis process being a fast Fourier transformation process, wherein the time length Tm determines a number of samples processed in the fast Fourier transformation process;
control processing circuitry configured to
determine whether image data regarding the subject, which is created based on the signal data upon which said signal-analysis process has been executed, includes a diagnostic target; and
change, to a different value, the time length Tm, based on a determination result of the control processing circuitry so that the time length Tm before the image data of the diagnostic target is created is different than the time length Tm after the image data of the diagnostic target is created; and
a display configured to display the image data regarding said subject based on the signal data that has been signal-analysis processed according to said time length Tm changed by the control processing circuitry,
wherein the Fourier processing circuitry is configured to execute the fast Fourier transformation process on the signal data using the time length Tm changed by the control processing circuitry.

2. The ultrasonic diagnostic device according to claim 1, wherein
said control processing circuitry is configured to change the value of said time length Tm when a predetermined instruction is inputted via a man-machine interface.

3. The ultrasonic diagnostic device according to claim 2, wherein
said predetermined instruction is an instruction for switching a display image from a dynamic image to a static image.

4. The ultrasonic diagnostic device according to claim 3, further comprising a memory configured to save the signal data before said signal-analysis process is applied,
wherein the control processing circuitry is further configured to control said Fourier processing circuitry to, when said predetermined instruction is inputted, perform said signal-analysis process to the signal data saved in said memory under the time length Tm that has been changed by said control processing circuitry, in order to create said image data.

5. The ultrasonic diagnostic device according to claim 1, wherein the control processing circuitry is further configured to
extract features based on said image data, and
determine whether said image data includes the diagnostic target based on whether the extracted features include features of the diagnostic target of said subject.

6. The ultrasonic diagnostic device according to claim 1, wherein the control processing circuitry is further configured to
automatically adjust a display state of a waveform, based on a size of the waveform included in said image data, and
determine whether said image data includes the diagnostic target based on whether an adjustment state by said control processing circuitry is stable.

7. The ultrasonic diagnostic device according to claim 1, wherein
said time length Tm of said signal data is used to calculate a spectrum at each time in the fast Fourier transformation process.

8. The ultrasonic diagnostic device according to claim 1, wherein said Fourier processing circuitry is configured to obtain waveform data by signal-analysis processing signal data regarding a state of a site of said subject.

9. The ultrasonic diagnostic device according to claim 1, wherein said Fourier processing circuitry is configured to perform the signal-analysis process to signal data regarding valve regurgitation of the heart.

10. The ultrasonic diagnostic device according to claim 1, wherein
said processing parameters include a display parameter that specifies a display state of waveform data included in said image data; and
said display is configured to display said waveform data in the display state indicated by said display parameter.

11. The ultrasonic diagnostic device according to claim 1, wherein said control processing circuitry changes the time length Tm so that the time length Tm before an image of the diagnostic target is created is longer than the time length Tm after the image of the diagnostic target is created.

12. A method of controlling an ultrasonic diagnostic device comprising:
executing a signal-analysis process on signal components having time length Tm among signal data that corresponds to an ultrasonic echo received from a subject, the signal-analysis process being a fast Fourier transformation process, wherein the time length Tm determines a number of samples processed in the fast Fourier transformation process;
determining, by a controller circuit of the ultrasonic diagnostic device, whether image data regarding the subject, which is created based on the signal data upon which said signal-analysis process has been executed, includes a diagnostic target;
changing to a different value, based on a determination result of the determining step, the time length Tm so that the time length Tm before the image data of the diagnostic target is created is different than the time length Tm after the image data of the diagnostic target is created; and
displaying the image data regarding said subject based on the signal data that has been signal-analysis processed according to said time length Tm changed in the changing step,
wherein the executing step includes executing the fast Fourier transformation process on the signal data using the time length Tm changed in the changing step.

13. The method of controlling an ultrasonic diagnostic device according to claim 12, wherein
the value of said time length Tm is changed when a predetermined instruction is inputted via a man-machine interface.

14. The method of controlling an ultrasonic diagnostic device according to claim 13, wherein said predetermined instruction is an instruction for switching a display image from a dynamic image to a static image.

15. The method of controlling an ultrasonic diagnostic device according to claim 14, further comprising:
saving the signal data before said signal-analysis process is applied; and
controlling said signal-analysis process to, when said predetermined instruction is inputted, perform said signal-analysis process to said saved signal data using the time length Tm that has been changed, in order to create said image data.

16. The method of controlling an ultrasonic diagnostic device according to claim 12, further comprising:
   extracting features based on said image data; and
   determining, based on whether the extracted features include features of the diagnostic target of said subject, whether said image data includes the diagnostic target.

17. The method of controlling an ultrasonic diagnostic device according to claim 12, further comprising:
   automatically adjusting a display state of a waveform based on a size of said waveform included in said image data; and
   determining, based on whether an adjustment state is stable, whether said image data includes the diagnostic target.

18. The method of controlling an ultrasonic diagnostic device according to claim 12, wherein
   said time length Tm of said signal data is used to calculate a spectrum at each time in the fast Fourier transformation process.

19. The method of controlling an ultrasonic diagnostic device according to claim 12, wherein waveform data is obtained from signal data regarding a state of a site of said subject by said signal-analysis process.

20. The method of controlling an ultrasonic diagnostic device according to claim 12, wherein said signal-analysis process is executed to signal data regarding valve regurgitation of the heart.

21. The method of controlling an ultrasonic diagnostic device according to claim 12, wherein
   said processing parameters include a display parameter that specifies a display state of waveform data included in said image data; and
   the displaying step includes displaying said waveform data in the display state indicated by said display parameter.

22. The ultrasonic diagnostic device according to claim 11, wherein said changing step comprises changing the time length Tm so that the time length Tm before an image of the diagnostic target is created is longer than the time length Tm after the image of the diagnostic target is created.

* * * * *